United States Patent [19]

Beach

[11] 4,136,678

[45] Jan. 30, 1979

[54] METHOD OF ADMITTING SOLUTIONS TO MEDICAL DRAINAGE OR IRRIGATION CONDUITS

[76] Inventor: Janet Beach, P.O. Box 409, Camden, Me. 04843

[21] Appl. No.: 719,187

[22] Filed: Aug. 31, 1976

[51] Int. Cl.² ............................................. A61B 19/00
[52] U.S. Cl. .................................. 128/1 R; 128/232; 134/22 C; 137/15; 222/94
[58] Field of Search .................... 128/232, 272, 272.3, 128/349 R, 214 D, 247, 350 R, DIG. 24, 230, 349 B, 349 BV, 1 R; 222/94; 134/22 C, 34; 137/15

[56] References Cited

U.S. PATENT DOCUMENTS

| 3,172,577 | 3/1965 | Hartung | 128/232 X |
| 3,545,671 | 12/1970 | Ross | 128/272 X |
| 3,554,256 | 1/1971 | Anderson | 128/272 X |
| 3,768,476 | 10/1973 | Raitto | 128/349 R X |
| 3,848,603 | 11/1974 | Throner | 138/349 R |
| 3,911,918 | 10/1975 | Turner | 128/227 X |
| 3,965,910 | 6/1976 | Fischer | 128/349 R |

FOREIGN PATENT DOCUMENTS 7337619  4/1975  Fed. Rep. of Germany ............ 222/94

*Primary Examiner*—Robert W. Michell
*Assistant Examiner*—Michael H. Thaler
*Attorney, Agent, or Firm*—William G. Rhines

[57] ABSTRACT

This invention relates to medical apparatus for such usages as urological irrigation, and in one embodiment comprises twin bags of solution, each of which has a valved orifice that may be removably connected in the mid-section of an irrigation tube, which may be folded over into contacting juxtaposition with each other and manually squeezed simultaneously so as to force solution through both the upper and the lower segments of the tube at the same time.

2 Claims, 3 Drawing Figures

METHOD OF ADMITTING SOLUTIONS TO MEDICAL DRAINAGE OR IRRIGATION CONDUITS

BACKGROUND OF THE INVENTION

A common medical procedure is to catheterize patients to facilitate the removal of urine from their bladders, and, as to bedridden patients in particular, to do so using a so-called "indwelling catheter", i.e., one which is placed in the bladder and left there, with removal being prevented by an internal "balloon" in the manner of a so-called "Foley Catheter" or other suitable device. Such a catheter may then be connected to a drainage tube which leads into a collection jar or sack. However, such drainage arrangements, particularly when left in situ for any appreciable length of time, tend to become obstructed and/or to become a source of infection to the bladder. For these reasons, it is desirable to be able to flush out the tube with various solutions designed to release blockages, disinfect surfaces, etc. This is usually done by a nurse disconnecting the drainage tube from the catheter, filling a syringe with solution and forcing it into the tube. This procedure, however, is messy and may even increase the chance of infection by disturbing microbe accumulation and by exposing the catheter end to germ sources.

Accordingly, it is an object of this invention to provide means for admitting solutions to medical drainage or irrigation conduits.

Another object of this invention is to provide such means in disposable form.

Yet another object is to provide such means suitable for the simultaneous admittance of solution into associated lengths of such conduits.

SUMMARY OF INVENTION

Desired objectives may be achieved through practice of this present invention which, in one embodiment comprises twin bags of solution, each of which has a valved orifice that may be removeably connected in the mid-section of an irrigation tube, which may be folded over into contacting justaposition with each other and manually squeezed simultaneously so as to force solution through both the upper and the lower segments of the tube at the same time.

DESCRIPTION OF DRAWINGS

This invention may be understood from the description which follows and from the attached drawings in which.

DESCRIPTION OF PREFERRED EMBODIMENTS

Figure 1:
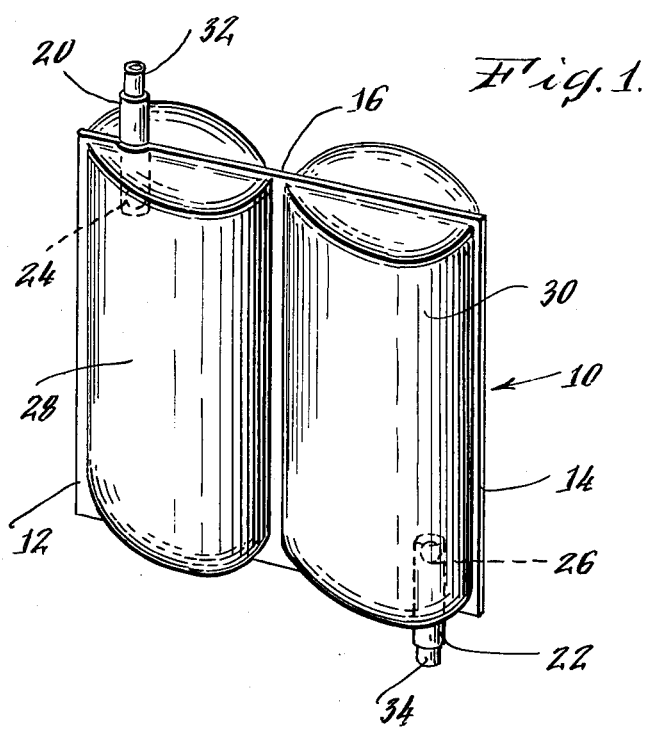
FIG. 1 depicts one embodiment of the present invention.

Referring first to FIG. #1, there is shown a twin-pack catheter or irrigation set 10 embodying the present invention. As shown, it comprises bags 12, 14 made from material which preferably is chemically stable and neutral, sterilizable, strong, impremeable to its contents, clear, and supple, such as 8 mil polyvinyl chloride. The pouches may also be imprintable and imprinted with instructions for use or other appropriate information.

The two pouches 12, 14 may be joined by a common hinge section 16 formed by heat bonding the layers of thermoplastic sheeting together. In a corner of each pouch, but facing in opposite directions from each other, are stopper valves 20, 22; each of which is made from plastic tubing, and has a ball 24, 26 inserted therein to serve as a pressure tight stopper against the passage therethrough of solution 28, 30 contained within the pouches 12, 14 respectively. Such solution may be water, saline, antiseptic, or otherwise desired composition. The outer ends 32, 34 respectively of the valves 20, 22 are adapted for receiving the ends of catheter tubes, drainage tubes, and the like (not shown), by known per se means such as annular rings or inclined planes.

Figure 2:
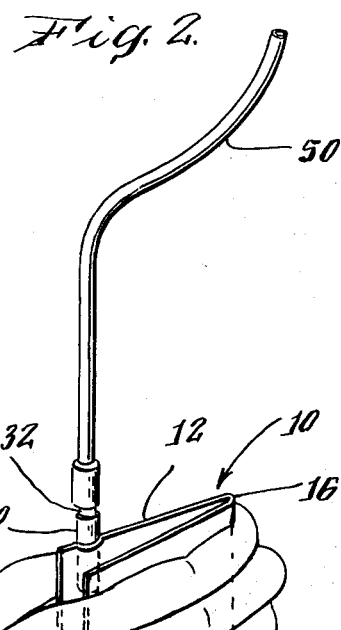
FIG. 2 depicts a manner of using the embodiment of the present invention shown in FIG. 1.

FIG. 2 illustrates a manner in which the embodiment of this invention shown in FIG. #1 may be used. The normal juncture between the catheter tube 50 and the drainage tube 52 having been broken, the twin-pack unit 10 is positioned therebetween, the catheter 50 is removeably affixed to the outer end 32 of the valve 20, the drainage tube 52 is removeably affixed to the outer end 34 of the valve 22, the inside ends of the valves 20, 22 are pinched between thumb and forefinger to pop the stopper balls 24, 26 out of the valves, the pouches 12, 14 are pivoted about the hinge 16 into contacting justaposition with each other, and the operator's hand 60 is used to manually squeeze both pouches. Simultaneously, solution will thereby be propelled upward through the catheter 50 and downward through the tube 52, following which, the tubes may be disconnected from the valves with which they respectively are associated, and reconnected to each other, following which the twin-pack may be discarded.

Figure 3:
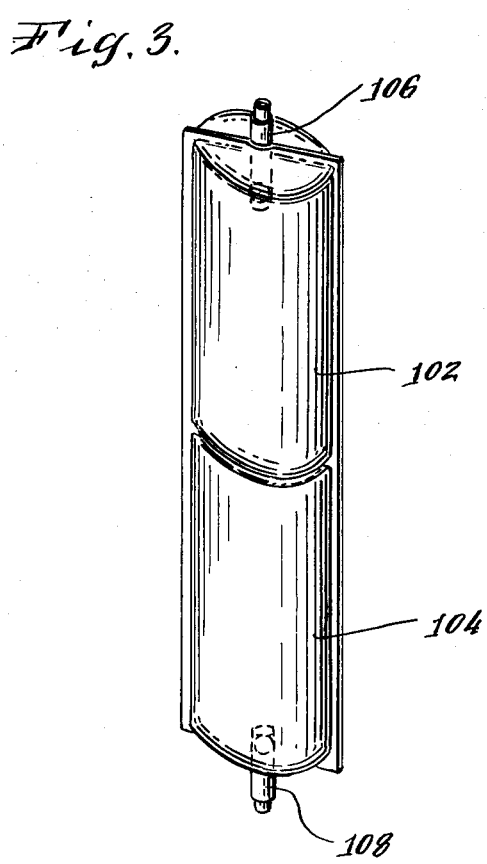
FIG. 3 depicts another embodiment of the present invention.

FIG. 3 illustrates another embodiment of the present invention, comprising tubelike containers, 102, 104 which are made from collapsible material and are positioned end to end, so that following a procedure of connecting the valves 104, 108 to associated catheter and drainage tubes, both containers may be manually squeezed at the same time to force the solutions contained therein in opposite directions.

It is to be understood that the embodiments of this invention herein as discussed and shown are by way of illustration and not of limitation, and that other embodiments may be made by those skilled in the cognizant arts without departing materially from the spirit or scope of this invention.

I claim:

1. A method of admitting solution from a first source into one of a pair of tubes which is connectable into tandem relationship with the other of said pair of tubes, concurrently with admitting solution from a second source into the other of said tubes comprising the steps of disconnecting said tubes from each other,
connecting one of said tubes to one of the egress means of apparatus comprising a pair of manually collapsible solution containers which are structurally integral with each other without a solution flowpath therebetween, each of which has a solution egress means, the egress means in each of said containers being positioned at the end thereof opposite the end of the other of said containers at which the egress means therein is positioned, wherein said containers are pouch-like and are structurally integrated with each other by means of a hinge-like juncture about which said containers may be swung into contact side-by-side with each other, connecting the other of said tubes to the other of said egress means, folding said containers over into side-by-side relationship, concurrently manually squeezing both of said containers, disconnecting both of said tubes from said egress means, and reconnecting said tubes to each other.

2. The method described in claim 1 including the step of rendering said egress means into condition for passing solution therethrough by manipulating valve means integral therewith prior to said manual squeezing step.

* * * * *